United States Patent [19]
Cai et al.

[11] Patent Number: 5,622,965
[45] Date of Patent: Apr. 22, 1997

[54] 4-HYDROXY-3-NITRO-1,2-DIHYDROQUINOLIN-2-ONES AND THE USE THEREOF AS EXCITATORY AMINO ACID AND GLYCINE RECEPTOR ANTAGONISTS

[75] Inventors: Sui X. Cai, Irvine; Eckard Weber, Laguna Beach, both of Calif.; John F. W. Keana, Eugene, Oreg.

[73] Assignees: State of Oregon, acting by and through The Oregon State Board of Higher Education, acting for and on behalf of The Oregon Health Sciences University and The University of Oregon, Eugene Oregon, Eugene, Oreg.; The Regents of the University of California, Oakland, Calif.

[21] Appl. No.: 101,244

[22] Filed: Aug. 2, 1993

Related U.S. Application Data

[63] Continuation-in-part of Ser. No. 30,608, Mar. 12, 1993, abandoned.

[51] Int. Cl.$^6$ .................. A61K 31/47; C07D 215/22; C07D 215/38
[52] U.S. Cl. .................. 514/312; 546/155; 546/157
[58] Field of Search .................. 546/155, 157; 514/312

[56] References Cited

U.S. PATENT DOCUMENTS

| | | | |
|---|---|---|---|
| 3,652,571 | 3/1972 | Sturm | 546/155 |
| 3,891,653 | 6/1975 | Dreikorn | 546/82 |
| 3,962,445 | 6/1976 | Buckle | 514/312 |
| 4,031,099 | 6/1977 | Buckle | 546/155 |
| 4,032,528 | 6/1977 | Hardtmann | 546/155 |
| 4,065,457 | 12/1977 | Buckle | 546/155 |
| 4,190,659 | 2/1980 | Hardtmann | 514/312 |
| 4,192,876 | 3/1980 | Hardtmann | 514/312 |
| 4,218,448 | 8/1980 | Aldrich et al. | 514/294 |
| 4,251,534 | 2/1981 | Aldrich et al. | 514/312 |
| 4,909,829 | 3/1990 | Theodoridis | 504/247 |
| 4,988,815 | 1/1991 | Andre et al. | 546/159 |
| 5,028,707 | 7/1991 | Nichols et al. | 546/156 |
| 5,376,748 | 12/1994 | Carling et al. | 546/158 |

FOREIGN PATENT DOCUMENTS

| | | |
|---|---|---|
| 0385630 | 9/1990 | European Pat. Off. |
| 0459561 | 12/1991 | European Pat. Off. |
| 0481676 | 4/1992 | European Pat. Off. |
| 0489458 | 6/1992 | European Pat. Off. |
| 1453863 | 10/1976 | United Kingdom |
| WO93/14067 | 7/1993 | WIPO |

OTHER PUBLICATIONS

McQuaid, J Med Chem, vol. 35, pp. 3423–3425, 1992.
Haley, Brain Research, vol. 518, pp. 218–226, 1990.
Boast, Brain Research, vol. 442, pp. 345–348, 1988.
Dickenson, Neurosc Lett, vol. 121, pp. 263–266, 1991.
Tricklebank, Eur J of Pharm, vol. 167, pp. 127–135, 1989.
Schoepp, J Neural Transm, vol. 85, pp. 131–143, 1991.
Buckle et al., "4–Hydroxy–3–nitrocarbostyrils and their pharmaceutical use," Chem. Abstr. 82:139976j (1975).
Boast et al., "The N–methyl–D–aspartate antagonists CGS 19755 and CPP reduce ischemic brain damage in gerbils", Brain Res. 442:345–348 (1988).
Brady et al., "Stereoisomers of N–Allylnormetazocine: Phencyclidine–Like Behavioral Effects in Squirrrel Monkeys and Rats", Science 215:178–180 (Jan. 1982).
Buckle et al., "4–Hydroxy–3–nitro–2–quinolones and Related Compounds as Inhibitors of Allergic Reactions", J. Med. Chem. 18:726–732 (1975).
Dickenson & Aydar, "Antagonism at the glycine site on the NMDA receptor reduces spinal nociception in the rat", Neuroscience Lett. 121:263–266 (1991).
Haley et al., "Evidence for spinal N–methyl–D–aspartate receptor involvement in prolonged chemical nociception in the rat", Brain Res. 518:218–226 (1990).
Johnson & Ascher, "Glycine potentiates the NMDA response in cultured mouse brain neurons", Nature 325:529–531 (Feb. 1987).
Kemp et al., "7–Chlorokynurenic acid is a selective antagonist at the glycine modulatory site of the N–methyl–D–aspartate receptor complex", Proc. Natl. Acad. Sci. USA 85:6547–6550 (Sep. 1988).
Koek et al., "MK–801, A Proposed Noncompetitive Antagonist of Excitatory Amino Acid Neurotransmission, Produces Phencyclidine–Like Behavioral Effects in Pigeons, Rats, and Rhesus Monkeys", J. Pharmacol. & Exp. Ther. 245:969–974 (1988).
McQaid et al., "3–Phenyl–4–hydroxyquinolin–2(1H)–ones: Potent and Selective Antagonists at the Strychnine–Insensitive Glycine Site on the N–Methyl–D–aspartate Receptor Complex", J. Med. Chem. 35:3423–3425 (1992).
Patel & Mehta, "Synthesis of 2,4–Dihydroxyquinolines Using Polyphosphoric Acid as the Cyclizing Agent", J. Sci. Industr. Res. 19B:436–438 (Nov. 1960).
Schoepp et al., "Neuroprotectant effects of LY 274614, a structurally novel systemically active competitive NMDA receptor antagonist", J. Neural. Trans. 85:131–143 (1991).

(List continued on next page.)

Primary Examiner—C. Warren Ivy
Assistant Examiner—D. Margaret M. Mach
Attorney, Agent, or Firm—Sterne, Kessler, Goldstein & Fox P.L.L.C.

[57] ABSTRACT

Methods of treating or preventing neuronal loss associated with stroke, ischemia, CNS trauma, hypoglycemia and surgery, as well as treating neurodegenerative diseases including Alzheimer's disease, amyotrophic lateral sclerosis, Huntington's disease and Down's syndrome, treating or preventing the adverse consequences of the hyperactivity of the excitatory amino acids, as well as treating anxiety, chronic pain, convulsions and inducing anesthesia are disclosed by administering to an animal in need of such treatment a substituted or unsubstituted 4-hydroxy-3-nitro-1,2-dihydroquinolin-2-one or pharmaceutically acceptable salts thereof which have high binding to the glycine receptor.

22 Claims, No Drawings

OTHER PUBLICATIONS

Skilling et al., "Differential Effects of C– and N–Terminal Substance P Metabolites on the Release of Amino Acid Neurotransmitters from the Spinal Cord: Potential Role in Nociception", *J. Neurosci.* 10:1309–1318 (Apr. 1990).

Tricklebank et al., "A role for receptors of N–methyl–D–aspartic acid in the discriminative stimulus properties of phencyclidine", *Eur. J. Pharmacol.* 141:497–501 (1987).

Tricklebank et al., "The behavioural effects of MK–801: a comparison with antagonists acting non–competitively and competitively at the NMDA receptor", *Eur. J. Pharmacol.* 167:127–135 (1989).

Willetts & Balster, "The Discriminative stimulus effects of N–Methyl–D–Aspartate Antagonists in Phencyclidine–Trained Rats", *Neuropharmacology* 27:1249–1256 (1988).

Zukin et al., "Behavioral and biochemical stereoselectivity of sigma opiate/PCP receptors", *Brain Res.* 294:174–177 (1984).

Lipton, New Engl. J. Med., vol. 30, pp. 613–622, 1994.

4-HYDROXY-3-NITRO-1,2-DIHYDROQUINOLIN-2-ONES AND THE USE THEREOF AS EXCITATORY AMINO ACID AND GLYCINE RECEPTOR ANTAGONISTS

The present invention was made with U.S. Government support under Grant No. NIDA DAO 6726 awarded by the National Institute of Health. Therefore, the U.S. Government has certain rights in the invention.

CROSS REFERENCE TO RELATED APPLICATION

The present application is a continuation-in-part of U.S. application Ser. No. 08/030,608, filed Mar. 12, 1993, now abandoned the contents of which are fully incorporated by reference herein.

FIELD OF THE INVENTION

The present invention is in the field of medicinal chemistry. In particular, the present invention relates to substituted and unsubstituted 4-hydroxy-3-nitro-1,2-dihydroquinolin-2-ones and pharmaceutically acceptable salts thereof and their use to treat or prevent neuronal degeneration associated with ischemia, pathophysiologic conditions associated with neuronal degeneration, convulsions, anxiety, chronic pain and to induce anesthesia.

BACKGROUND OF THE INVENTION

Glutamate is thought to be the major excitatory neurotransmitter in the brain. There are three major subtypes of glutamate receptors in the CNS. These are commonly referred to as kainate, AMPA and N-methyl-D-aspartate (NMDA) receptors (Watkins and Olverman, *Trends in Neurosci.* 7:265–272 (1987)). NMDA receptors are found in the membranes of virtually every neuron in the brain. NMDA receptors are ligand-gated cation channels that allow $Na^+$, $K^+$ and $Ca^{++}$ to permeate when they are activated by glutamate or aspartate (non-selective, endogenous agonists) or by NMDA (a selective, synthetic agonist) (Wong and Kemp, *Ann. Rev. Pharmacol. Toxicol.* 31:401–25 (1991)).

Glummate alone cannot activate the NMDA receptor. In order to become activated by glummate, the NMDA receptor channel must first bind glycine at a specific, high affinity glycine binding site which is separate from the glutamate/NMDA binding site on the receptor protein (Johnson and Ascher, *Nature* 325:329–331 (1987)). Glycine is therefore an obligatory co-agonist at the NMDA receptor/channel complex (Kemp, J. A., et al., *Proc. Natl. Acad. Sci. USA* 85:6547–6550 (1988)).

Besides the binding sites for glutamate/NMDA and glycine, the NMDA receptor carries a number of other functionally important binding sites. These include binding sites for $Mg^{++}$, $Zn^{++}$, polyamines, arachidonic acid and phencyclidine (PCP) (Reynolds and Miller, *Adv. in Pharmacol.* 21:101–126 (1990); Miller, B., et al., *Nature* 355:722–725 (1992)). The PCP binding site—now commonly referred to as the PCP receptor—is located inside the pore of the ionophore of the NMDA receptor/channel complex (Wong, E. H. F., et al., *Proc. Natl. Acad. Sci. USA* 83:7104–7108 (1986); Huettner and Bean, *Proc. Natl. Acad. Sci. USA* 85:1307–1311 (1988); MacDonald, J. F., et al., *Neurophysiol.* 58:251–266 (1987)). In order for PCP to gain access to the PCP receptor, the channel must first be opened by glutamate and glycine. In the absence of glummate and glycine, PCP cannot bind to the PCP receptor although some studies have suggested that a small amount of PCP binding can occur even in the absence of glummate and glycine (Sircar and Zukin, *Brain Res.* 556:280–284 (1991)). Once PCP binds to the PCP receptor, it blocks ion flux through the open channel. Therefore, PCP is an open channel blocker and a non-competitive glummate antagonist at the NMDA receptor/channel complex.

One of the most potent and selective drugs that bind to the PCP receptor is the anticonvulsant drug MK-801. This drug has a $K_d$ of approximately 3 nM at the PCP receptor (Wong, E. H. F., et al., *Proc. Natl. Acad. Sci. USA* 83:7104–7108 (1986)).

Both PCP and MK-801 as well as other PCP receptor ligands [e.g. dextromethorphan, ketamine and N,N,N'-trisubstituted guanidines] have neuroprotective efficacy both in vitro and in vivo (Gill, R., et at., *J. Neurosci.* 7:3343–3349 (1987); Keana, J. F. W., et al., *Proc. Natl. Acad. Sci. USA* 86:5631–5635 (1989); Steinberg, G. K., et al., *Neuroscience Lett.* 89:193–197 1988); Church, J., et al., In: *Sigma and Phencyclidine-Like Compounds as Molecular Probes in Biology*, Domino and Kamenka, eds., Ann Arbor: NPP Books, pp. 747–756 (1988)). The well-characterized neuroprotective efficacy of these drugs is largely due to their capacity to block excessive $Ca^{++}$ influx into neurons through NMDA receptor channels which become over activated by excessive glutamate release in conditions of brain ischemia (e.g. in stroke, cardiac arrest ischemia etc.) (Collins, R. C., *Metabol. Br. Dis.* 1:231–240 (1986); Collins, R. C., et al., *Annals Int. Med.* 110:992–1000 (1989)).

However, the therapeutic potential of these PCP receptor drugs as ischemia rescue agents in stroke has been severely hampered by the fact that these drugs have strong PCP-like behavioral side effects (psychotomimetic behavioral effects) which appear to be due to the interaction of these drugs with the PCP receptor (Tricklebank, M. D., et al., *Eur. J. Pharmacol.* 167:127–135 (1989); Koek, W., et al., *J. Pharmacol. Exp. Ther.* 245:969 (1989); Willels and Balster, Neuropharmacology 27:1249 (1988)). These PCP-like behavioral side effects appear to have caused the withdrawal of MK801 from clinical development as an ischemia rescue agent. Furthermore, these PCP receptor ligands appear to have considerable abuse potential as demonstrated by the abuse liability of PCP itself.

The PCP-like behavioral effects of the PCP receptor ligands can be demonstrated in animal models: PCP and related PCP receptor ligands cause a behavioral excitation (hyperlocomotion) in rodents (Tricklebank, M. D., et al., *Eur. J. Pharmacol.* 167:127–135 (1989))and a characteristic katalepsy in pigeons (Koek, W., et al., *J. Pharmacol. Exp. Ther.* 245:969 (1989); Willets and Balster, *Neuropharmacology* 27:1249 (1988)); in drug discrimination paradigms, there is a strong correlation between the PCP receptor affinity of these drugs and their potency to induce a PCP-appropriate response behavior (Zukin, S. R., et al., *Brain Res.* 294:174 (1984); Brady, K. T., et al., *Science* 215:178 (1982); Tricklebank, M. D., et al., *Eur. J. Pharmacol.* 141:497 (1987)).

Drugs acting as competitive antagonists at the glutamate binding site of the NMDA receptor such as CGS 19755 and LY274614 also have neuroprotective efficacy because these drugs-like the PCP receptor ligands—can prevent excessive $Ca^{++}$ flux through NMDA receptor/channels in ischemia (Boast, C. A., et al., *Brain Res.* 442:345–348 (1988); Schoepp, D. D., et al., *J. Neural. Trans.* 85:131–143 (1991)). However, competitive NMDA receptor antagonists also have PCP-like behavioral side-effects in animal models (behavioral excitation, activity in PCP drug discrimination tests) although not as potently as MK-801 and PCP (Tricklebank, M. D., et al., *Eur. J. Pharmacol.* 167:127–135 (1989)).

An alternate way of inhibiting NMDA receptor channel activation is by using antagonists at the glycine binding site of the NMDA receptor. Since glycine must bind to the glycine site in order for glutamate to effect channel opening (Johnson and Ascher, *Nature* 325:329–331 (1987); Kemp, J. A., et al., *Proc. Natl. Acad. Sci. USA* 85:6547–6550 (1988)), a glycine antagonist can completely prevent ion flux through the NMDA receptor channel—even in the presence of a large amount of glutamate.

Recent in vivo microdialysis studies have demonstrated that in the rat focal ischemia model, there is a large increase in glutamate release in the ischemic brain region with no significant increase in glycine release (Globus, M. Y. T., et al., *J. Neurochem.* 57:470–478 (1991)). Thus, theoretically, glycine antagonists should be very powerful neuroprotective agents, because they can prevent the opening of NMDA channels by glutamate non-competitively and therefore-unlike competitive NMDA antagonists—do not have to overcome the large concentrations of endogenous glutamate that are released in the ischemic brain region.

Furthermore, because glycine antagonists act at neither the glutamate/NMDA nor the PCP binding sites to prevent NMDA channel opening, these drugs might not cause the PCP-like behavioral side effect seen with both PCP receptor ligands and competitive NMDA receptor antagonists (Tricklebank, M. D., et at., *Eur. J. Pharmacol.* 167:127–135 (1989); Koek, W., et al., *J. Pharmacol. Exp. Ther.* 245:969 (1989); Willets and Balster, *Neuropharmacology* 27:1249 (1988); Tricklebank, M. D., et al., *Eur. J. Pharmacol* 167:127–135 (1989); Zukin, S. R., et al., *Brain Res.* 294:174 (1984); Brady, K. T., et al., *Science* 215:178 (1982); Tricklebank, M. D., et al., *Eur. J. Pharmacol.* 141:497 (1987)). That glycine antagonists may indeed be devoid of PCP-like behavioral side effects has been suggested by recent studies in which available glycine antagonists were injected directly into the brains of rodents without resulting in PCP-like behaviors (Tricklebank, M. D., et al., *Eur. J. Pharmacol.* 167:127–135 (1989)).

However, there have been two major problems which have prevented the development of glycine antagonists as clinically useful neuroprotective agents:

A. Most available glycine antagonists with relatively high receptor binding affinity in vitro such as 7-Cl-kynurenic acid (Kemp, J. A., et al., *Proc. Natl. Acad. Sci. USA* 85:6547–6550 (1988)), 5,7-dichlorokynurenic acid (McNamara, D., et al., *Neuroscience Lett.* 120:17–20 (1990)) and indole-2-carboxylic acid (Gray, N. M., et al., *J. Med. Chem.* 34:1283–1292 (1991)) cannot penetrate the blood/brain barrier and therefore have no utility as therapeutic agents;

B. The only widely available glycine antagonist that sufficiently penetrates the blood/brain barrier—the drug HA-966 (Fletcher and Lodge, *Eur. J. Pharmacol.* 151:161–162 (1988))—is a partial agonist with micromolar affinity for the glycine binding site. A neuroprotective efficacy for HA-966 in vivo has not been demonstrated nor has it been demonstrated for the other available glycine antagonists because they lack bioavailability in vivo.

A need continues to exist for potent and selective glycine/NMDA antagonists which can penetrate the blood/brain barrier and which:

lack the PCP-like behavioral side effects common to the PCP-like NMDA channel blockers such as MK801 or to the competitive NMDA receptor antagonists such as CGS19755;

show potent anti-ischemic efficacy because of the non-competitive nature of their glutamate antagonism at the NMDA receptor;

have utility as novel anticonvulsants with fewer side-effects than the PCP-like NMDA channel blockers or the competitive NMDA antagonists;

help in defining the functional significance of the glycine binding site of the NMDA receptor in vivo.

There have been a number of reports in the literature regarding the preparation of 4-hydroxy-3-nitro-1,2-dihydroquinolin-2-ones. U.K. Patent No. 1,453,863, published Oct. 27, 1976, discloses the preparation of compounds having the formula:

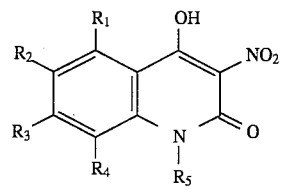

wherein $R_1$, $R_2$, $R_3$ and $R_4$ are hydrogen, alkyl, alkoxy, aryloxy, aralkoxy, aryl, aralkyl, heterocyclic, hydroxy, nitro, or a halogen group. Particular compounds disclosed in this U.K. patent include 3-nitro-4-hydroxy-1,2-dihydroquinolin-2-one, 3,6-dinitro-4-hydroxy-1,2-dihydroquinolin-2-one, 4-hydroxy-3,6,8-trinitro-1,2-dihydroquinolin-2-one, 6,7-dimethyl-4-hydroxy-3-nitroquinolin-2-one, 6,7-diethyl-4-hydroxy-3-nitro-1,2-dihydroquinolin-2-one, 7,8-dimethyl-4-hydroxy-3-nitro-1,2-dihydroquinolin-2-one, 4-hydroxy-8-methyl-3-nitro-1,2-dihydroquinolin-2-one, 6-ethyl-4-hydroxy-3-nitro-1,2-dihydroquinolin-2-one, 6-chloro-4-hydroxy-3-nitro-1,2-dihydroquinolin-2-one, 4-hydroxy-6-methyl-3-nitro-1,2-dihydroquinolin-2-one, 6-ethyl-4-hydroxy-3-nitro-1,2-dihydroquinolin-2-one, 4-hydroxy-5-methyl-3-nitro-1,2-dihydroquinolin-2-one, 4-hydroxy-7-methyl-3-nitro-1,2-dihydroquinolin-2-one, 4-hydroxy-8-methyl-3-nitro-1,2-dihydroquinolin-2-one, 6-bromo-4-hydroxy-3-nitro-1,2-dihydroquinolin-2-one, 5,8-dimethyl-4-hydroxy-3-nitro-1,2-dihydroquinolin-2-one, 5,7-dimethyl-4-hydroxy-3-nitro-1,2-dihydroquinolin-2-one6,8-dimethylo4-hydroxy-3-nitro-1,2-dihydroquinolin-2-one, 7,8-dimethyl-4-hydroxy-3-nitro-1,2-dihydroquinolin-2-one, 8-bromo-4-hydroxy-3-nitro-1,2-dihydroquinolin-2-one, 8-chloro-4-hydroxy-3-nitro-1,2-dihydroquinolin-2-one, 7-chloro-4-hydroxy-3-nitro-1,2-dihydroquinolin-2-one, 4-hydroxy-7-methoxy-3-nitro-1,2-dihydroquinolin-2-one, 4-hydroxy-7-methoxy-6-methyl-3-nitro-1,2-dihydroquinolin-2-one, 8-ethoxy-4-hydroxy-3-nitro-6-n-propyl-1,2-dihydroquinolin-2-one, 4-hydroxy-7-methyl-8-n-propoxy-3-nitro-1,2-dihydroquinolin-2-one, 4-hydroxy-3-nitro-7-phenoxy-1,2-dihydroquinolin-2-one, 7-benzyloxy-4-hydroxy-6-methyl-3-nitro-1,2-dihydroquinolin-2-one, 7-ethyl-4-hydroxy-3-nitro-6-phenyl-1,2-dihydroquinolin-2-one, 8-benzyl-4-hydroxy-6-methyl-3-nitro-1,2-dihydroquinolin-2-one, 4-hydroxy-6-methyl-3-nitro-7-(3'-pyridyl)-1,2-dihydroquinolin-2-one, 4-hydroxy-3-nitro-8-(3'-pyridyl)-1,2-dihydroquinolin-2-one, 4,7-dihydroxy-3-nitro-1,2-dihydroquinolin-2-one, 4-hydroxy-3-nitro-7-n-propoxy-1,2-dihydroquinolin-2-one, and 7-chloro-4-hydroxy-6-methoxy-3-nitro-1,2-dihydroquinolin-2-one.

According to U.K. Patent No. 1,453,863, the 4-hydroxy-3-nitro-1,2-dihydroquinolin-2-ones are useful for the inhibition of the effects of certain types of antigen-antibody reactions and are useful for the prophylaxis and treatment of diseases associated with allergic or immunological reactions, e.g., asthma, hay fever and rhinitis. See also,. French Patent No. 2,229,414, Published Dec. 13, 1974 and German Patent No. 2,424,076, Published Dec. 5, 1974.

U.S. Pat. No. 4,192,876, issued Mar. 11, 1980, discloses compounds having the formula:

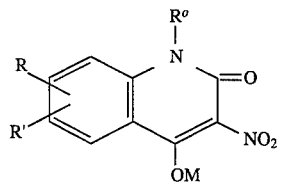

wherein $R^o$ is hydrogen, alkyl of 1 to 6 carbon atoms, alkenyl of 3 to 6 carbon atoms, alkynyl of 3 to 6 carbon atoms, cycloalkyl of 3 to 6 carbon atoms, cycloalkylalkyl in which the cycloalkyl is of 3 to 6 carbon atoms and the alkyl portion is of 1 or 2 carbon atoms, or

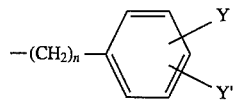

M is hydrogen or a cation derived from a proton abstracting agent, n is 0 or 1,

Y and Y' are independently hydrogen, halo of atomic weight of from 18 to 80, i.e., fluoro, chloro or bromo, alkyl of 1 to 3 carbon atoms, alkoxy of 1 to 3 carbon atoms or trifluoromethyl, and R and R' are independently hydrogen, halo of atomic weight of from 18 to 80, i.e., fluoro, chloro, or bromo, alkyl of 1 to 4 carbon atoms, alkoxy of 1 to 4 carbon atoms, nitro or trifluoromethyl, or R and R' together form 6,7-methylenedioxy, with the proviso that only one of R and R' can be from the group consisting of nitro and trifluoromethyl, with the further proviso that the unsaturation in any alkenyl or alkynyl is on other than the alpha carbon atom. Particular compounds disclosed in this patent include 6-trifluoromethyl-4-hydroxy-3-nitro-1,2-dihydroquinolin-2-one and 8-methyl-4-hydroxy-3-1,2 -dihydroquinolin-2-one. According to this patent, the disclosed compounds are useful in the treatment of allergic conditions, e.g., allergic asthma.

U.S. Pat. No. 4,988,815, Issued Jan. 29, 1991, discloses compounds having the formula:

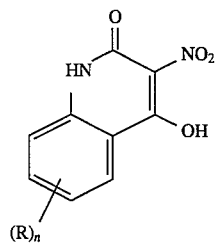

wherein R is lower alkoxy, halogen and lower alkyl and n is an integer from 0 to 2. These compounds are reportedly useful as intermediates for the preparation of 1H-imidazo [4,5-c]quinolines European Patent Application Publication No. 0,385,630, discloses the use of 4-hydroxy-3-nitro-1,2-dihydroquinolin-2-one compounds as intermediates for the preparation of 1H-imidazo[4,5-c]quinolin-4-amines.

Buckle, D. R., et al., J. Med. Chem. 18:726732 (1975), discloses substituted 4-hydroxy-3-nitro-1,2-dihydroquinolin-2-ones having the formula:

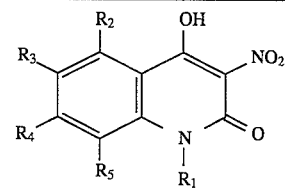

| Compd | $R_1$ | $R_2$ | $R_3$ | $R_4$ | $R_5$ |
|---|---|---|---|---|---|
| 8a | H | H | H | H | H |
| 8b | H | Me | H | H | H |
| 8c | H | Me | H | Me | H |
| 8d | H | Me | H | H | Me |
| 8e | H | H | Me | H | H |
| 8f | H | H | Et | H | H |
| 8g | H | H | Br | H | H |
| 8h | H | H | Cl | H | H |
| 8i | H | H | $NO_2$ | H | H |
| 8j | H | H | Me | Me | H |
| 8k | H | H | Me | H | Me |
| 8l | H | H | Et | Et | H |
| 8m | H | H | H | Me | H |
| 8n | H | H | H | Me | Me |
| 8o | H | H | H | H | Me |
| 8p | H | H | H | H | Br |
| 8q | H | H | H | H | Cl |
| 8r | Me | H | H | H | H |
| 8s | Et | H | H | H | H |
| 8t | Ph | H | H | H | H |
| 8u | Me | H | Me | H | H |
| 8v | Et | H | Me | H | H |
| 8w | Me | H | Cl | H | H |
| 8x | Et | H | Cl | H | H |
| 8y | Me | H | Me | Me | H |
| 8z | Me | H | H | Cl | H |

These compounds are reportedly useful as inhibitors of allergic reactions.

U.S. Pat. No. 5,028,707, issued Jul. 2, 1991, discloses compounds of the formula:

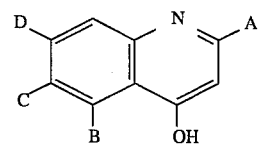

wherein A is azide, amide or isocyanate, B is chloro or hydrogen, C is methoxy or hydrogen and D is chloro, bromo, iodo or fluoro. These compounds reportedly are useful as photoaffinity probes for the NMDA receptor complex on neurons.

McQuaid, L. A. et al., J. Med. Chem. 35:3423–3425 (1992), discloses 3-phenyl-4-hydroxy-1,2-dihydroquinolin-2-ones having the formula:

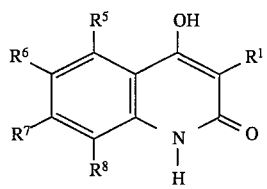

| no. | $R_1$ | $R_2$ | $R_3$ |
|-----|-------|-------|-------|
| 7a  | H     | H     | H     |
| 7b  | Cl    | Cl    | H     |
| 7c  | Cl    | Cl    | $CH_3$ |
| 7d  | Cl    | Cl    | $CH_3O$ |
| 7e  | Cl    | Cl    | $NO_2$ |
| 7f  | Cl    | Cl    | OH    |
| 7g  | Cl    | Cl    | $NH_2$ | which are reported to be selective antagonists at the strychnine-insensitive glycine site on the NMDA receptor complex.

European Patent Application Publication No. 489,458, discloses compounds having the formula:

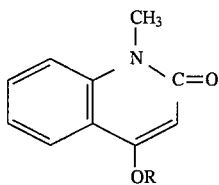

wherein $R^1$ represents a group of formula (i), (ii) or (iii):

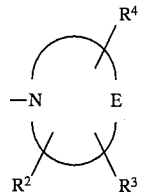  (i)

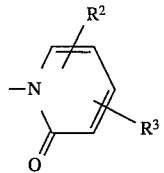  (ii)

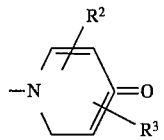  (iii)

in which the E represents the residue of a 5-membered heteroaromatic ring containing 0, 1, 2, or 3 further nitrogen atoms. These compounds are reportedly useful in the treatment and/or prevention of conditions, in particular neurodegenerative disorders, which require the administration of selective non-competitive antagonists of NMDA receptors.

U.S. Pat. No. 4,032,528, issued Jun. 28, 1977, discloses compounds of the formula:

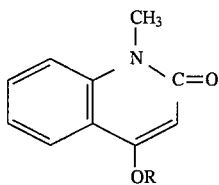

wherein R is alkyl of 4 to 6 carbon atoms. These compounds are reportedly useful as tranquilizers and as anti-convulsant agents.

European Patent Application Publication No. 459,561, Published Dec. 12, 1991, discloses 2,4-dioxo-1,2,3,4-tetrahydroquinoline derivatives having the formula:

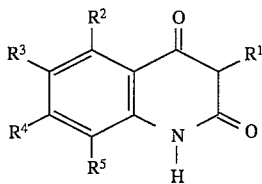  I wherein
$R^1$ is a group of part formula (i) or (ii):

$$-(CH=CH)_n-T$$

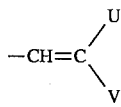

These compounds are reported to be selective non-competitive antagonists of NMDA receptors and are useful in treating neurodegenerative disorders, convulsions and schizophrenia.

SUMMARY OF THE INVENTION

The invention relates to a method of treating or preventing neuronal loss associated with stroke, ischemia, CNS trauma, hypoglycemia and surgery, as well as treating neurodegenerative diseases including Alzheimer's disease, amyotrophic lateral sclerosis, Huntington's disease and Down's syndrome, treating or preventing the adverse consequences of the overstimulation of the excitatory amino acids, as well as treating anxiety, convulsions, chronic pain and inducing anesthesia, comprising administering to an animal in need of such treatment a compound of the Formula (I)

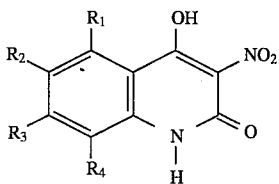  I or a pharmaceutically acceptable salt thereof;
wherein
$R_1$–$R_4$ may be hydrogen, nitro, amino, halo, haloalkyl, cyano, alkyl, alkenyl, alkynyl, azido, acylamino, sulfonyl, aryl or alkoxy.

The present invention resulted from the initial discovery that 4-hydroxy-3-nitro-1,2-dihydroquinolin-2-one exhibits high binding to the glycine receptor. Since 4-hydroxy-3-nitro-1,2-dihydroquinolin-2-one is highly selective for the glycine receptor, it is expected that the compounds of the present invention may not exhibit the PCP-like behavioral side effects common to the PCP-like NMDA channel blockers such as MK-801 and other NMDA antagonists such as CGS19755. Thus, the compounds of the present invention are useful for treating pathophysiologic conditions, without significant side effects or toxicity.

DESCRIPTION OF THE PREFERRED EMBODIMENTS

The present invention relates to substituted and unsubstituted 4-hydroxy-3-nitro-1,2-dihydroquinolin-2-ones which are highly selective, competitive antagonists of the glycine binding site of the NMDA receptor and of the excitatory amino acids. The 4-hydroxy-3-nitro-1,2-dihydroquinolin-2-ones which may be employed in the practice of the invention have the following Formula (I):

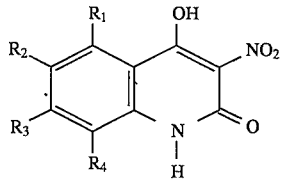

or a pharmaceutically acceptable salt thereof;
wherein $R_1$–$R_4$ may be hydrogen, nitro, amino, halo, haloalkyl, cyano, alkyl, alkenyl, alkynyl, azido, acylamino, sulfonyl, aryl or alkoxy.

Preferred compounds within the scope of Formula I are wherein $R_1$ is nitro, amino, chloro or bromo; $R_2$ is hydrogen, chloro, bromo or trifluoromethyl; $R_3$ is nitro, chloro, bromo or trifluoromethyl; and $R_4$ is hydrogen, nitro, chloro, bromo or amino.

Typical $C_{6-14}$ aryl groups include phenyl, naphthyl, phenanthryl, anthracyl, indenyl, azulenyl, biphenyl, biphenylenyl and fluorenyl groups.

Typical amino groups include NH2, $NHR_5$ and $NR_5R_6$, wherein $R_5$ and $R_6$ are $C_{1-4}$ alkyl groups.

Typical halo groups include fluorine, chlorine, bromine and iodine.

Typical $C_{1-4}$ alkyl groups include methyl, ethyl, propyl, isopropyl, butyl, sec.-butyl, and tert.-butyl groups.

Typical $C_{2-4}$ alkenyl groups include vinyl, allyl, 1-butenyl, 2-butenyl, 3-butenyl, and isobutenyl groups.

Typical $C_{2-4}$ alkynyl groups include propargyl, 1-propynyl, 2-propynyl, 1-butynyl, 2-butynyl and 3-butynyl groups.

Typical haloalkyl groups include $C_{1-4}$ alkyl groups substituted by one or more fluorine, chlorine, bromine or iodine atoms, e.g. fluoromethyl, difluoromethyl, trifluoromethyl, pentafluoroethyl, 1,1-difluoroethyl and trichloromethyl groups.

Typical alkoxy groups include oxygen substituted by one of the $C_{1-4}$ alkyl groups mentioned above.

Particularly preferred compounds of the present invention include, but are not limited to 4-hydroxy-3-nitro-1,2-dihydroquinolin-2-one, 5,7-dichloro-4-hydroxy-3-nitro-1,2'-dihydroquinolin-2-one, 5,7-dichloro-4-hydroxy-3,6-dinitro-1,2-dihydroquinolin-2-one, 5,7-dichloro-4-hydroxy-3,8-dinitro-1,2-dihydroquinolin-2-one, 5-chloro-7-trifluoromethyl-4-hydroxy-3,6-dinitro-1,2-dihydroquinolin-2-one, 5-chloro-7-trifluoromethyl-4-hydroxy-3-nitro-1,2-dihydroquinolin-2-one, 5-bromo-7-trifluoromethyl-4-hydroxy-3-nitro-1,2-dihydroquinolin-2-one, 5,6,7-trichloro-4-hydroxy-3-nitro-1,2-dihydroquinolin-2-one, 6,7-dichloro-4-hydroxy-3,5-dinitro-1,2-dihydroquinolin-2-one, 6,7-dichloro-4-hydroxy-3,8-dinitro-1,2-dihydroquinolin-2-one, 6,7-dibromo-4-hydroxy-3,5-dinitro-1,2-dihydroquinolin-2-one, 6,7-dibromo-4-hydroxy-3,8-dinitro-1,2-dihydroquinolin-2-one, 6,7-difluoro-4-hydroxy-3,5-dinitro-1,2-dihydroquinolin-2-one, 5,7-bis(trifluoromethyl)-4-hydroxy-3-nitro-1,2-dihydroquinolin-2-one, 5-(trifluoromethyl)-6-chloro-4-hydroxy-3-nitro-1,2-dihydroquinolin-2-one, 5-(trifluoromethyl)-6-bromo-4-hydroxy-3-nitro-1,2-dihydroquinolin-2-one, 5-(trifluoromethyl)-6-fluoro-4-hydroxy-3-nitro-1,2-dihyroquinolin-2-one, 6-chloro-7-(trifluoromethyl)-4-hydroxy-3-nitro-1,2-dihydroquinolin-2-one, 6-bromo-7-(trifluoromethyl)-4-hydroxy-3-nitro-1,2-dihyroquinolin-2-one, 6-fluoro-7-(trifluoromethyl)-4-hydroxy-3-nitro-1,2-dihydroquinolin-2-one, 6-chloro-7-(trifluoromethyl)-4-hydroxy-3,5-dinitro-1,2-dihydroquinolin-2-one, 6-bromo-7-(trifluoromethyl)-4-hydroxy-3,5-dinitro-1,2-dihydroquinolin-2-one, 6-fluoro-7-(trifluoromethyl)-4-hydroxy-3,5-dinitro-1,2-dihydroquinolin-2-one, 5,7-dibromo-4-hydroxy-3,6-dinitro-1,2-dihydroquinolin-2-one, 5,7-difluoro-4-hydroxy-3,6-dinitro-1,2-dihydroquinolin-2-one, · 5,7-bis(trifluoromethyl)-4-hydroxy-3,6-dinitro-1,2-dihydroquinolin-2-one, 5,7-bis(trifluoromethyl)-6-chloro-4-hydroxy-3-nitro-1,2-dihydroquinolin-2-one, 5,7-bis(trifluoromethyl)-6-bromo-4-hydroxy-3-nitro-1,2-dihydroquinolin-2-one, 5,7-bis(trifluoromethyl)-6-fluoro-4-hydroxy-3-nitro-1,2-dihydroquinolin-2-one, 5,7-bis(trifluoromethyl)-6-azido-4-hydroxy-3-nitro-1,2-dihydroquinolin-2-one, 5,7-bis(trifluoromethyl)-6-acetamido-4-hydroxy-3-nitro-1,2-dihydroquinolin-2-one, 6,7,8-trichloro-4-hydroxy-3-nitro-1,2-dihydroquinolin-2-one, 5,7-dimethyl-4-hydroxy-3-nitro-1,2-dihydroquinolin-2-one, 5,6,7,8-tetrafluoro-4-hydroxy-3-nitro-1,2-dihydroquinolin-2-one, 6,7,8-trifluoro-4-hydroxy-3,5-dinitro-1,2-dihydroquinolin-2-one, 7-chloro-6,8-difluoro-4-hydroxy-3,5-dinitro-1,2-dihydroquinolin-2-one, 6,7-dichloro-8-fluoro-4-hydroxy-3,5-dinitro-1,2-dihydroquinolin-2-one, 5,7-dichloro-6-bromo-4-hydroxy-3-nitro-1,2-dihydroquinolin-2-one, 5,7-dichloro-6-fluoro-4-hydroxy-3-nitro-1,2 -dihydroquinolin-2-one, 5,7-dichloro-6-azido-4-hydroxy-3-nitro-1,2-dihydroquinolin-2-one, 5,7-dichloro-6-acetamido-4-hydroxy-3-nitro-1,2-dihydroquinolin-2-one, 5,7-dibromo-6-chloro-4-hydroxy-3-nitro-1,2-dihydroquinolin-2-one, 5,7-dibromo-6-fluoro-4-hydroxy-3-nitro-1,2-dihydroquinolin-2-one, and 5,7-dibromo-6-azido-4-hydroxy-3-nitro-1,2-dihydroquinolin-2-one.

Certain of the compounds of the present invention are expected to be potent anticonvulsants in animal models and will prevent ischemia-induced nerve cell death in the gerbil global ischemia model after i.p. administration.

The compounds of the present invention are active in treating or preventing neuronal loss, neurodegenerative diseases, chronic pain, are active as anticonvulsants and inducing anesthesia. Certain of the compounds of the present invention are expected to exhibit little or no untoward side effects caused by non-selective binding with other receptors, particularly, the PCP and glutamate receptors associated with the NMDA receptor. In addition, certain of the compounds block kainate, AMPA and quisqualate receptors and are therefore useful as broad-spectrum excitatory amino acid receptor antagonists. Moreover, the compounds of the present invention are effective in treating or preventing the adverse consequences of the hyperactivity of the excitatory amino acids, e.g. those which are involved in the NMDA receptor system, by blocking the glycine receptors and preventing the ligand-gated cation channels from opening and allowing excessive influx of $Ca^{++}$ into neurons, as occurs during ischemia.

Neurodegenerative diseases which may be treated with the compounds of the present invention include those selected from the group consisting of Alzheimer's disease, amyotrophic lateral sclerosis, Huntington's disease and Down's syndrome.

The compounds of the present invention find particular utility in the treatment or prevention of neuronal loss associated with multiple strokes which give rise to dementia. After a patient has been diagnosed as suffering from a stroke, the compounds of the present invention may be administered to ameliorate the immediate ischemia and prevent further neuronal damage that may occur from recurrent strokes.

Moreover, the compounds of the present invention are able to cross the blood/brain barrier which makes them particularly useful for treating or preventing conditions involving the central nervous system.

The compounds of the invention find particular utility in treating or preventing the adverse neurological consequences of surgery. For example, coronary bypass surgery requires the use of heart-lung machines which tend to introduce air bubbles into the circulatory system which may lodge in the brain. The presence of such air bubbles robs neuronal tissue of oxygen, resulting in anoxia and ischemia. Pre- or post- surgical administration of the 4-hydroxy-3-nitro-1,2-dihydroquinolin-2-ones of the present invention will treat or prevent the resulting ischemia. In a preferred embodiment, the compounds of the invention are administered to patients undergoing cardiopulmonary bypass surgery or carotid endarterectomy surgery.

The compounds of the present invention also find utility in treating or preventing chronic pain. Such chronic pain may be the result of surgery, trauma, headache, arthritis, or other degenerative disease. The compounds of the present invention also find particular utility in the treatment of phantom pain that results from amputation of an extremity. In addition to treatment of pain, the compounds of the invention are also expected to be useful in inducing anesthesia, either general or local anesthesia, for example, during surgery.

The glycine and excitatory amino acid antagonists may be tested for in vivo anticonvulsant activity after intraperitoneal injection using a number of anticonvulsant tests in mice (audiogenic seizure model in DBA-2 mice, pentylenetetrazol-induced seizures in mice, NMDA-induced death). The compounds may also be tested in drug discrimination tests in rats trained to discriminate PCP from saline. It is expected that most of the compounds of the present invention will not generalize to PCP at any dose. In addition, it is also expected that none of the compounds will produce a behavioral excitation in locomotor activity tests in the mouse. It is expected that such results will suggest that the glycine, AMPA, kainate and quisqualate antagonists of the present invention do not show the PCP-like behavioral side effects that are common to NMDA channel blockers such as MK-801 and PCP or to competitive NMDA antagonists such as CGS19755.

The glycine and excitatory amino acid antagonists are also expected to show potent activity in vivo after intraperitoneal injection suggesting that these compounds can penetrate the blood/brain barrier.

The compounds of the present invention may be tested for potential glycine antagonist activity by observing the inhibition of binding of 1 μM glycine-stimulated [$^3$H]-MK-801 in rat or guinea pig brain membrane homogenates. The more potent the glycine antagonist, the less [3H]-MK-801 can bind since the [$^3$H]-MK801 binding site (PCP receptor) is accessible only upon opening of the ion channel by glutamate and glycine (Fletcher, E. L., et at., in *Glycine Neurotransmission*, Otterson, P., et al. (eds.), John Wiley and Sons (1990); Johnson, J. W., et al., *Nature* 325:529 (1987)).

The compounds of the present invention may be prepared by the general methods taught in U.K. Patent No. 1,453,863. In particular, the compounds having Formula I are prepared by nitration of the corresponding 4-hydroxy-1,2-dihydroquinolin-2-one with one of the following:

(i) nitrous fumes generated with concentrated nitric acid and arsenic oxide;

(ii) acetic acid plus concentrated nitric acid;

(iii) fuming nitric acid in chloroform; or (iv) concentrated nitric acid.

The starting 4-hydroxy-1,2-dihydroquinolin-2-ones may be prepared by standard methods known in the literature. For example, the method of Patel and Mehta (*J. Sci. Ind. Res.* 19B:436–8 (1960)) may be employed where an appropriately substituted aniline is condensed with diethyl malonate followed by hydrolysis of the monoanilide and cyclization with polyphosphoric acid. With symmetrically substituted anilines or those substituted at one ortho position, only one product results from cyclization. With asymmetric anilines with both ortho positions free, varying proportions of 5- and 7- substituted hydroxy-1,2-dihydroquinolin-2-ones result, Thus, with 3,4-dimethylaniline, a 1:1 mixture of two possible isomers results. With bulkier substituents, the ratio is influenced in favor of the newly formed C—C bond being furthest from the largest substituent(s). Thus, 3,4-diethylaniline results predominantely in the production of the 6,7-diethyl-1,2-dihydroquinolin-2-one and only small amounts of the 5,6-isomer. See, U.K. Patent No. 1,453,863, the contents of which are fully incorporated by reference herein.

3-Nitro-4-hydroxy-1,2-dihydroquinolin-2-one 16a (Buckle, D. R., et al., *J. Med. Chem.* 18:726–732 (1975)) was prepared by nitration of 2,4-dihydroxyquinolin 15a (Scheme I, eq 6). Compound 16a was found to have a $K_i$ value of 18 μM with a potency of 1.4% of 5,7-dichlorokynurenic acid (DCK). Further nitration of 16a gave mono-nitro subtituted compound 16b, which was found to be about as active as 16a. 5,7-Dichloro-2,4-dihydroxyquinoline 15c was prepared by reaction of 3,5-dichloroaniline with diethyl malonate followed by basic hydrolysis and cyclization in polyphosphoric acid (PPA) (eq 7). Patel, G. H., et al., *J. Sci. Industr. Res.* 19B:436–438 (1960). Nitration of 15c gave 5,7-dichloro-3-nitro-4-hydroxy-1,2-dihydroquinolin-2-one 16c which was found to have a $K_i$ value of 1.4 μM with a potency of 19% of DCK. The binding ability of these nitro compounds to glycine/NMDA receptor is very similar to quinoxalinedione (QX) compounds (QX 2% of DCK, 5,7-dichloro-QX, 20% of QX). Thus, the series of 3-nitro-4-hydroxy-1,2-dihydroquinolin-2-ones provides some promising antagonists which bind to the glycine/NMDA receptor.

Scheme I

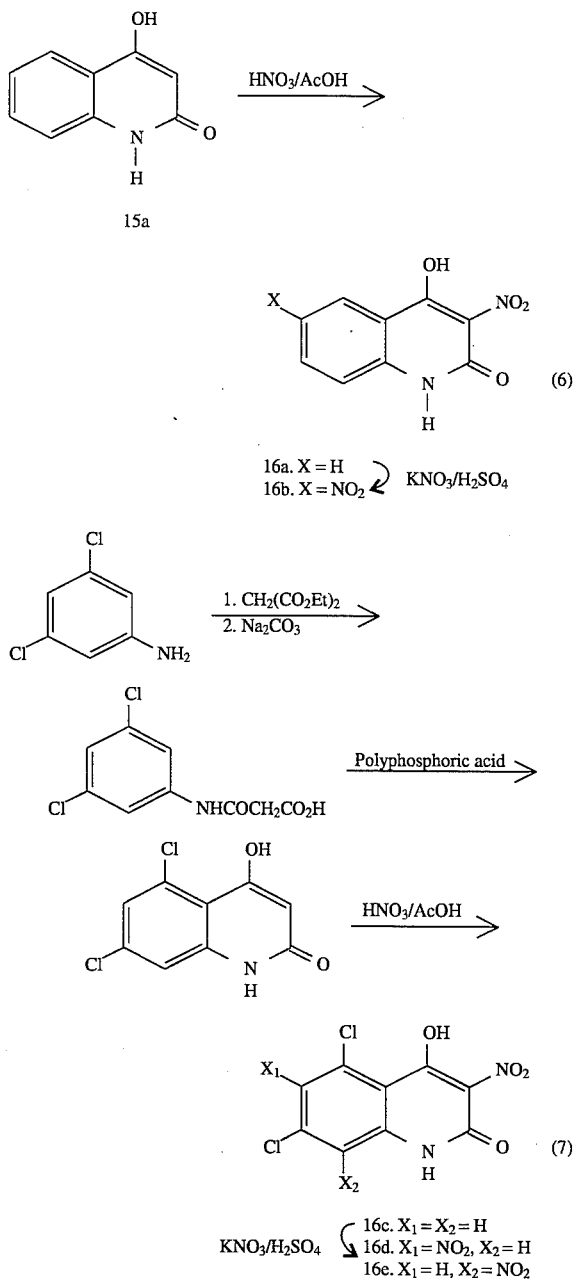

Additional dichloro and dichloronitro-substituted 3-nitro-4-hydroxy-1,2-dihydroquinolin-2-ones were also prepared. Nitration of 5,7-dichloro-3-nitro-4-hydroxy-1,2-dihydroquinolin-2-one 16c gave a mixture of 16d and 16e with the nitro position undetermined (Scheme I). A mixture of about 1:1 of 6,7-dichloro-2,4-dihydroxyquinoline 15f and 5,6-dichloro-2,4-dihydroxyquinoline 15g were obtained by reaction of 3,4-dichloroaniline with diethyl malonate under similar conditions as that of 15c (Scheme II, eq 8). An attempt to separate 15f and 15g by fractional precipitation of a basic solution of 15f and 15g via addition of aqueous HCl failed and these two compounds did not separate well in TLC. Surprisingly, nitration of the mixture of 15f and 15g resulted in a precipitate from the reaction mixture which was found to be 5,6-dichloro-3-nitro-4-hydroxy-1,2-dihydroquinolin-2-one 16f ($K_i$=0.8 μM) with no contamination of the other isomer. Further nitration of 16f give a single dinitro product which is either 16h or 16i.

Scheme II

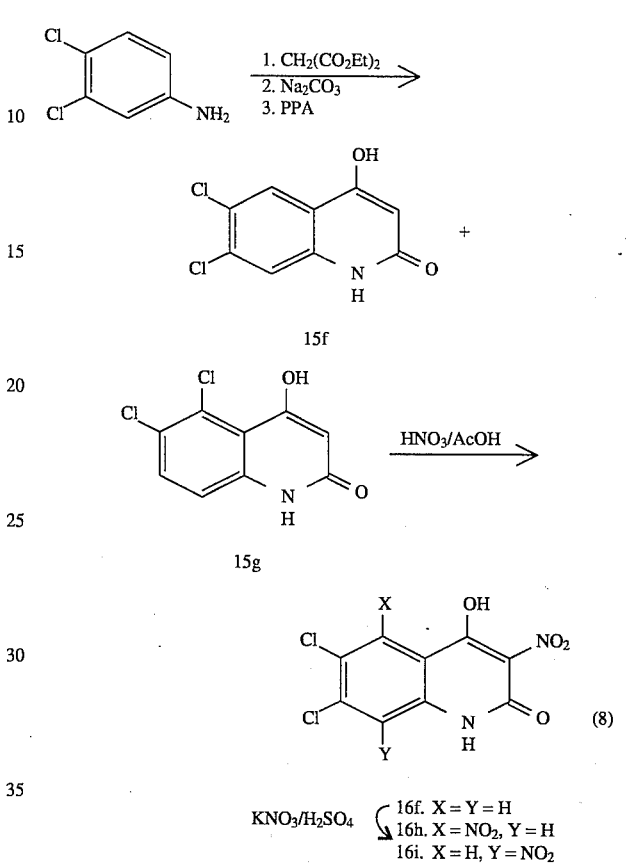

Thus, the present invention is directed to compounds having high binding to the glycine receptor and low binding to the kainate and AMPA sites. Particular compounds of the invention may have high antagonist potency at the kainate, AMPA and quisqualate receptors in addition to the glycine receptor. According to the present invention, those compounds having high binding to the glycine receptor exhibit a glycine binding affinity ($K_i$) of about 100 μM or less in a glycine binding assay. Preferably, the compounds of the present invention exhibit a $K_i$ of 10 μM or less. Most preferably, the compounds of the present invention exhibit a $K_i$ of 1 μM or less. The compounds exhibit high binding to the kainate and AMPA sites if they exhibit a $K_i$ of about 10 μM or less, especially, 1 μM or less in a kainate or AMPA binding assay.

The glycine antagonist potency in vitro may be determined using a 1 μM glycine-stimulated [$^3$H]-MK801 binding assay. This assay takes advantage of the fact that the binding of [$^3$H]-MK801 to the PCP receptor inside the pore of the NMDA channel is dependent on the presence of both glutamate and glycine. In the absence of glycine but in the presence of glutamate, [$^3$H]-MK801 cannot bind effectively to the PCP receptor, because the NMDA channel remains closed and access of [$^3$H]-MK801 to the PCP receptor inside the closed channel pore is severely restricted.

The assay is conducted using rat brain membrane homogenates which are enriched in NMDA receptors. The membranes are prepared as follows. Frozen rat brains obtained from Pel-Freez, Rogers, Arkansas) are homogenized in 15 volumes (w/v) of ice cold 0.32M sucrose. The homogenate is spun at 1,000×g for ten minutes. The supernatant is collected and spun for 20 minutes at 44,000×g. The pellet is suspended in 15 volumes of water (relative to original brain weight). The homogenate is again spun at 44,000×g for twenty minutes. The pellet is resuspended in 5 volumes of water and the suspension is freeze-thawed 2 times. After the final thaw cycle, the suspension is brought to 15 volumes with water and spun at 44,000×g for twenty minutes. The pellet is resuspended in 5 volumes of ice-cold 10 mM HEPES, and is titrated to pH 7.4 with KOH containing 0.04% Triton X-100. Membranes are incubated with the Triton/HEPES buffer at 37° C. for 15 minutes. The volume is then brought to 15 with ice-cold 10 mM HEPES, pH 7.4, and spun/washed three times with spins of 44,000×g between washes. The final pellet is suspended in three volumes of 50 mM HEPES, pH 7.4 and the protein concentration is determined with a standard dye-binding protein assay (Bio-Rad, Richmond, Calif.). The suspension is stored at-80° C. until used. Only HPLC grade water is used for all buffers and suspensions/washings. The extensive washings are necessary to remove as much endogenous glycine from the membrane preparation as possible.

On the day of the assay, the previously prepared membranes are thawed and 5 mM Tris/HCl buffer, pH 7.4, is added to yield a final protein concentration of 0.156 mg/ml. For binding assays, 0.8 ml of membranes are piperted into polypropylene tubes followed by 0.033 ml of 15.1 µM 5,7-dichlorokynurenic acid (DCK), 0.033 ml of 30.3 µM glycine in buffer (or buffer alone), 0.033 ml of 303 tim glutamate in buffer (or for controls, 0.1 ml 1 mM PCP instead of DCK/gly/glu), 0.033 ml glycine antagonist in buffer (or buffer alone) and 0.1 ml buffer containing 200,000 cpm [3H]-MK801. Nonspecific binding is defined as the difference in binding that occurs in the absence or presence of PCP (final concentration: 100 µM). To determine the effect of 1 µM glycine on the binding of [3H]-MK801, bound radioactivity in the presence of 10 µM glutamate alone (final concentration) is subtracted from the bound radioactivity in the presence of both 10 µM glummate and 1 µM glycine (final concentration). A 500 nM concentration (final) of 5,7-dichlorokynurenic (DCK) acid is added to all assay tubes. This concentration of the glycine antagonist DCK "buffers" most of the residual endogenous glycine that is not removed by the extensive washing steps that are carried out during the membrane preparation procedure. The 500 nM DCK does not interfere with the stimulation of [$^3$H]-MK801 binding that is effected by the addition of 1 µM exogenous glycine.

The assays are incubated for 120 minutes at room temperature after which time the membrane-bound radioactivity is isolated from the free radioactivity by vacuum filtration through Whatman glass fiber filters that had been pretreated with 0.3% polyethyleneimine. Filtration is accomplished using a Brandel 48 well cell harvester. Filtered membranes are washed three times with 3 ml each of ice cold buffer. Filters are transferred to scintillation vials and 5 ml of scintillation cocktail is added. The vials are shaken overnight and the radioactivity is counted by liquid scintillation spectroscopy. The assays are done in triplicate and all experiments are conducted at least three times.

Inhibition dose response curves are constructed using increasing concentrations of glycine antagonists from 5 nM to 330 µM. $IC_{50}$ values are determined for compounds active in inhibiting 1 µM glycine-stimulated [$^3$H]-MK801 binding by computer-assisted plotting of the inhibition curves and interpolation. When compounds are found to inhibit glycine-stimulated [$^3$H]-MK801 binding, experiments are conducted to determine whether the inhibition of the glycine-stimulated [$^3$H]-MK801 binding is indeed mediated at the glycine binding site of the NMDA receptor. In these experiments, a fixed concentration of antagonist sufficient to produce a >95% inhibition of the 1 µM glycine-stimulated [$^3$H]-MK801 binding is incubated with the membranes without any additional glycine (above 1 µM) and in the presence of increasing concentrations of additional glycine (2 µM to 1 µM). If the inhibition of [3H]-MK801 binding by the drug in the presence of 1 µM glycine is fully reversed by adding increasing concentrations of glycine, then the inhibition of [3H]-MK801 binding is mediated by the drug acting as an antagonist at the glycine binding site of the NMDA receptor.

After constructing inhibition dose response curves and determination of glycine reversibility, $K_i$ values for the glycine antagonists are calculated using the Cheng and Prusoff equation employing the experimentally determined $IC_{50}$ values, the known concentration of glycine in the assay (1 µM) and the known affinity of glycine for the glycine binding site of the NMDA receptor (100 nM).

The same rat brain membrane homogenates used for the 1 µM glycine -stimulated [$^3$H]-MK801 binding assay are used for the [$^3$H]-AMPA radioligand binding assay. On the day of the assay the frozen membranes (prepared as described above) are thawed and diluted with 30mM Tris/HCl buffer containing 2.5 mM $CaCl_2$ and 100 mM KSCN, pH 7.4, to yield a final membrane concentration of 1.25 mg/ml membrane protein. For the binding assay, 0.8ml of membrane homogenate is added to polypropylene tubes followed by 0.033 ml drug and 0.067 ml buffer (or for controls by 0.1 ml buffer alone) and 0.1 ml buffer containing 200,000 cpm of [$^3$H]-AMPA. The assay is incubated for 30 minutes on ice. Bound radioactivity is separated from free radioactivity by filtration over Whatman glass fiber filters (pretreated with 0.3% polyethyleneimine) using a Brandel 48 well cell harvester.

Filtered membranes are washed three times with 3 ml each of ice cold buffer. The filters are transferred to scintillation vials and 5 ml of scintillation cocktail is added. The vials are shaken overnight and radioactivity is counted by liquid scintillation spectroscopy. Nonspecific binding is determined by the radioactivity that remains bound to the membranes in the presence 10 mM glummate. Inhibition dose response curves are constructed by adding increasing concentrations of drug from 10 nM to 100 µM.

The same membrane preparation as that used for the [$^3$H]-AMPA binding assay may be used for the [3H]-Kainate radioligand binding assay. On the day of the assay the frozen rat brain membranes are thawed and 5 mM Tris/HCl buffer, pH 7.4, is added to yield a final concentration of 0.5 mg/ml membrane protein. For the binding assay, 0.8 ml of membrane homogenate is added to polypropylene tubes followed by 0.033 ml drug and 0.067 ml buffer (or for controls by 0.1 ml buffer alone) and 0.1 ml buffer containing 200,000 cpm of [3H]-kainate. The assay is incubated for 2 hours on ice. Bound radioactivity is separated from free radioactivity by filtration over Whatman glass fiber filters (pretreated with 0.3% polyethyleneimine) using a Brandel 48 well cell harvester. Filtered membranes are washed three times with 3 ml each of ice cold buffer. The filters are transferred to scintillation vials and 5 ml of scintillation cocktail is added. The vials are shaken overnight and radioactivity is counted by liquid scintillation spectroscopy. Nonspecific binding is determined by the radioactivity that remains bound to the membranes in the presence 10 mM glutamate. Inhibition dose response curves are constructed by adding increasing concentrations of drug from 250 nM to 330 µM.

The anxiolytic activity of any particular compound of the present invention may be determined by use of any of the recognized animal models for anxiety. A preferred model is described by Jones, B. J. et al., *Br. J. Pharmacol.* 93:985–993 (1988). This model involves administering the compound in question to mice which have a high basal level of anxiety. The test is based on the finding that such mice find it aversive when taken from a dark home environment in a dark testing room and placed in an area which is painted white and brightly lit. The test box has two compartments, one white and brightly illuminated and one black and non-illuminated. The mouse has access to both compartments via an opening at floor level in the divider between the two compartments. The mice are placed in the center of the brightly illuminated area. After locating the opening to the dark area, the mice are free to pass back and forth between the two compartments. Control mice tend to spend a larger proportion of time in the dark compartment. When given an anxiolytic agent, the mice spend more time exploring the more novel brightly lit compartment and exhibit a delayed latency to move to the dark compartment. Moreover, the mice treated with the anxiolytic agent exhibit more behavior in the white compartment, as measured by exploratory rearings and line crossings. Since the mice can habituate to the test situation, naive mice should always be used in the test. Five parameters may be measured: the latency to entry into the dark compartment, the time spent in each area, the number of transitions between compartments, the number of lines crossed in each compartment, and the number of rears in each compartment. The administration of the compounds of the present invention is expected to result in the mice spending more time in the larger, brightly lit area of the test chamber.

In the light/dark exploration model, the anxiolytic activity of a putative agent can be identified by the increase of the numbers of line crossings and rears in the light compartment at the expense of the numbers of line crossings and rears in the dark compartment, in comparison with control mice.

A second preferred animal model is the rat social interaction test described by Jones, B. J. et al., supra, wherein the time that two mice spend in social interaction is quantified. The anxiolytic activity of a putative agent can be identified by the increase in the time that pairs of male rats spend in active social interaction (90% of the behaviors are investigatory in nature). Both the familiarity and the light level of the test arena may be manipulated. Undrugged rats show the highest level of social interaction when the test arena is familiar and is lit by low light. Social interaction declines if the arena is unfamiliar to the rats or is lit by bright light. Anxiolytic agents prevent this decline. The overall level of motor activity may also be measured to allow detection of drug effects specific to social behaviors.

The efficacy of the glycine and excitatory amino acid antagonists to inhibit glutamate neurotoxicity in rat brain cortex neuron cell culture system may be determined as follows. An excitotoxicity model modified after that developed by Choi (Choi, D. W., *J. Neuroscience* 7:357 (1987)) may be used to test anti-excitotoxic efficacy of the glycine and excitatory amino acid antagonists. Fetuses from rat embryonic day 19 are removed from time-mated pregnant rats. The brains are removed from the fetuses and the cerebral cortex is dissected. Cells from the dissected cortex are dissociated by a combination of mechanical agitation and enzymatic digestion according to the method of Landon and Robbins (*Methods in Enzymology* 124:412 (1986)). The dissociated cells are passed through a 80 micron nitex screen and the viability of the cells are assessed by Trypan Blue. The cells are plated on poly-D-lysine coated plates and incubated at 37° C. in an atmosphere containing 91% $O_2$/9% $CO_2$. Six days later, fluoro-d-uracil is added for two days to suppress non-neural cell growth. At culture day 12, the primary neuron cultures are exposed to 100 μM glutamate for 5 minutes with or without increasing doses of glycine and excitatory amino acid antagonist or other drugs. After 5 minutes the cultures are washed and incubated for 24 hours at 37° C. Neuronal cell damage is quantitated by measuring lactate dehydrogenase (LDH) activity that is released into the culture medium. The LDH activity is measured according to the method of Decker et al. (Decker et al., *J. Immunol. Methods* 15:16 (1988)).

The anticonvulsant activity of the glycine and excitatory amino acid antagonists may be assessed in the audiogenic seizure model in DBA-2 mice as follows. DBA-2 mice may be obtained from Jackson Laboratories, Bar Harbor, Me. These mice at an age of <27 days develop a tonic seizure within 5–10 seconds and die when they are exposed to a sound of 14 kHz (sinus wave) at 110 dB (Lonsdale, D., *Dev. Pharmacol. Ther.* 4:28 (1982)). Seizure protection is defined when animals injected with drug 30 minutes prior to sound exposure do not develop a seizure and do not die during a 1 minute exposure to the sound. 21 day old DBA-2 mice are used for all experiments. Compounds are given intraperitoneally in either saline, DMSO or polyethyleneglycol-400. Appropriate solvent controls are included in each experiment. Dose response curves are constructed by giving increasing doses of drug from 1 mg/kg to 100 mg/kg. Each dose group (or solvent control) consists of at least six animals.

The anticonvulsant efficacy of the glycine receptor antagonists may be assessed in the pentylenetetrazol (PTZ)-induced seizure test as follows. Swiss/Webster mice, when injected with 50 mg/kg PTZ (i.p.) develop a minimal clonic seizure of approximately 5 seconds in length within 5–15 minutes after drug injection. Anticonvulsant efficacy of a glycine/excitatory amino acid antagonist (or other) drug is defined as the absence of a seizure when a drug is given 30 minutes prior to PTZ application and a seizure does not develop for up to 45 minutes following PTZ administration. Glycine/excitatory amino acid antagonist or other drugs are given intraperitoneally in either saline, DMSO or polyethyleneglycol-400. Appropriate solvent controls are included in each experiment. Dose response curves are constructed by giving increasing doses of drug from 1 mg/kg to 100 mg/kg. Each dose group (or solvent control) consists of at least six animals.

The efficacy of glycine/excitatory amino acid antagonists to protect mice from NMDA-induced death may be assessed as follows. When mice are injected with 200 mg/kg N-methyl-D-aspartate (NMDA) i.p., the animals will develop seizures followed by death within 5–10 minutes. Glycine/excitatory amino acid antagonists are tested for their ability to prevent NMDA-induced death by giving the drugs i.p. 30 minutes prior to the NMDA application. Glycine/excitatory amino acid antagonist or other drugs are given intraperitoneally in either saline, DMSO or polyethyleneglycol-400. Appropriate solvent controls are included in each experiment. Dose response curves are constructed by giving increasing doses of drug from 1 mg/kg to 100 mg/kg. Each dose group (or solvent control) consists of at least six animals.

A series of different evaluations may be conducted on doses of the glycine/excitatory amino acid antagonists of the invention to determine the biological activity of the compounds both in normal gerbils and in animals exposed to 5 minutes of bilateral carotid occlusion. See Scheme I.

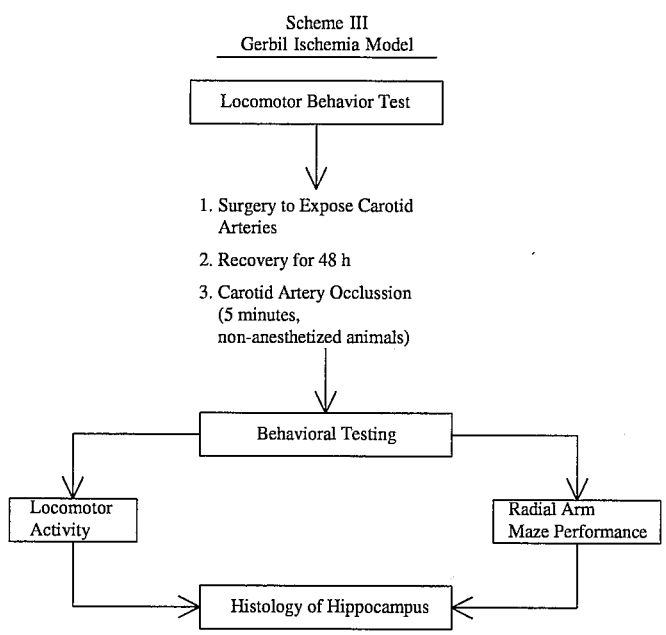

Scheme III
Gerbil Ischemia Model

These studies are conducted in animals who are conscious and have no other pharmacological agents administered to them. Gerbils are preinstrumented 48-hours prior to ischemia to allow for the complete elimination of the pentobarbital anesthetic which is employed. When tested with drugs, animals are given IP injections of the glycine/ excitatory amino acid antagonist or vehicle. In the case of multiple injections, animals are given IP injections 2 hours apart and the final injection is given 30 minutes prior to the ischemic period or in the case of post treatment, the animals are given injections at 30 minutes, 2 hours, 4 hours and 6 hours post-ischemic reperfusion.

In order to assess the direct pharmacological activity or potential activity of the glycine/excitatory amino acid antagonists, naive gerbils are injected with either saline or differing doses of the antagonist. The behavioral changes are assessed using a photobeam locomotor activity chamber which is a two foot circular diameter arena with photobeam detection. Animals are individually placed in the 2 foot diameter chambers. The chambers are housed in a cabinet which is closed and noise is abated using both a background white noise generator and a fan. Animals are placed in these chambers in the case of the initial pharmacological evaluation for a period of 6 hours and the total activity during each successive hour is accumulated using the computer control systems.

Saline results in an initial high rate of activity, with the control animals showing a first hour activity level of about 1600 counts. This level of control activity is typical for the gerbil under these experimental conditions. As the session progressed, animals decrease their exploratory activity and at the terminal period the activity declines to about 250 counts per hour. It is expected that the glycine/excitatory amino acid antagonists of the present invention will have no significant effect on either the initial exploratory rate or the terminal rate of exploration.

In a next phase of the evaluation of the glycine/excitatory amino acid antagonists, gerbils are pretreated with varying doses of the antagonists and then exposed to a five minute period of bilateral carotid occlusion. Following the initiation of reperfusion, animals are placed into the circular locomotor activity testing apparatus and the activity at the beginning of the first hour following reperfusion is monitored for the subsequent four hours.

Control animals not exposed to ischemia and given injections of saline prior to being placed in the locomotor activity chamber show a characteristic pattern of activity which in the first hour of locomotor activity is substantially higher than during all other hours and progressively declined over the four hours to a very low value. In contrast to the progressive decline in activity over the four hour testing period, control animals that are exposed to five minutes of cortical ischemia demonstrate a completely different pattern of locomotor activity. During the first hour there is a significant decline in activity which is followed by a progressive increase in which the activity during the fourth hour is ten-fold higher than that demonstrated by animals not exposed to carotid occlusion. These results are typical and are a reliable result of the alterations caused by five minutes of bilateral carotid occlusion in the gerbil.

Separate groups of gerbils are pretreated with the glycine/ excitatory amino acid antagonists of the invention 30 minutes before the onset of carotid occlusion and then placed into the locomotor activity following one hour of reperfusion. It is expected that pretreatment of the gerbils with the glycine/excitatory amino acid antagonists of the invention will prevent both the post-ischemic decrease and increase in activity. Post-ischemic decreases in activity are expected to be near zero during the first hour following reperfusion. Pretreatment with the glycine/excitatory amino acid antagonists of the invention is expected to reduce or prevent this early depression of behavior. In addition, the glycine/excitatory amino acid antagonists of the invention are expected to prevent the post-ischemic stimulation of behavior.

Subsequent to completion of the single dose pretreatment evaluations, gerbils are also evaluated with multiple injections of the glycine/excitatory amino acid antagonists of the invention. Doses are administered I.P. at 6 hours, 4 hours, 2 hours and 30 minutes prior to the onset of 5 minutes of ischemia.

At 24 hours all animals are evaluated for differences in patrolling behavior using a 8-arm radial maze. In this procedure, animals are placed into the center start chamber of the maze, the barrier removed and the amount of time and the number of times the animal makes an error recorded prior to completion of exploration in all 8 arms of the maze. An error is defined as the revisiting of an arm by entering to the extent of the entire body without including tail by the animal. If the animal perseveres or fails to leave the arm for longer than five minutes, the session is terminated. In the control population of the animals, the number of errors and exploration of the maze with no prior experience (naive) is approximately 6 errors. This is an average value for an N of 28 gerbils. Following 5 minutes of bilateral carotid occlusion and testing at 24 hours, gerbils make an average number of errors of 21. When animals are pretreated with the glycine/excitatory amino acid antagonists of the invention, there is expected to be a significant reduction in the number of errors made. There is also expected to be a significant sparing of the behavioral changes that are induced in the radial arm maze performance.

It is also expected that post treatment the glycine/excitatory amino acid antagonists of the invention will reduce the short term memory impairment 24 hours post ischemic/reperfusion.

The effects of 5 minutes of bilateral carotid occlusion on neuronal cell death in the dorsal hippocampus may be evaluated in animals 7 days after ischemia reperfusion injury. Previous studies have demonstrated that neuronal degeneration begins to occur around 3 days following cerebral ischemia. By 7 days those neurons which have been affected and will undergo cytolysis and have either completed degeneration or are readily apparent as dark nuclei and displaced nuclei with eosinophilic cytoplasm with pycnotic nuclei. The lesion with 5 minutes of ischemia is essentially restricted within the hippocampus to the CA1 region of the dorsal hippocampus. The intermedial lateral zone of the horn is unaffected and the dentate gyrus and/or in CA3 do not show pathology. Gerbils are anesthetized on day 7 following ischemia with 60 mg/kg of pentobarbital. Brains are perfused transcardiac with ice-cold saline followed by buffered paraformaldehyde (10%). Brains are removed, imbedded and sections made. Sections are stained with hematoxylin-eosin and neuronal cell counts are determined in terms of number of neuronal nuclei/100 micrometers. Normal control animals (not exposed to ischemia reperfusion injury) will not demonstrate any significant change in normal density nuclei within this region. Exposure to five minutes of bilateral carotid occlusion results in a significant reduction in the number of nuclei present in the CA1 region. In general, this lesion results in a patchy necrosis instead of a confluent necrosis which is seen if 10 minutes of ischemia is employed. Pretreatment with the glycine receptor antagonists of the invention are expected to produce a significant protection of hippocampal neuronal degeneration.

It is known that NMDA receptors are critically involved in the development of persistent pain following nerve and tissue injury. Tissue injury such as that caused by injecting a small amount of formalin subcutaneously into the hindpaw of a test animal has been shown to produce an immediate increase of glutamate and aspartate in the spinal cord (Skilling, S. R., et al., *J. Neurosci.* 10:1309–1318 (1990)). Administration of NMDA receptor blockers reduces the response of spinal cord dorsal horn neurons following formalin injection (Dickenson and Aydar, *Neuroscience Lett.* 121:263–266 (1991); Haley, J. E., et al., *Brain Res.* 518:218–226 (1990)). These dorsal horn neurons are critical in carrying the pain signal from the spinal cord to the brain and a reduced response of these neurons is indicative of a reduction in pain perceived by the test animal to which pain has been inflicted by subcutaneous formalin injection.

Because of the observation that NMDA receptor antagonists can block dorsal horn neuron response induced by subcutaneous formalin injection, NMDA receptor antagonists have potential for the treatment of chronic pain such as pain which is caused by surgery or by amputation (phantom pain) or by infliction of other wounds (wound pain). However, the use of conventional NMDA antagonists such as MK801 or CGS 19755, in preventing or treating chronic pain, is severely limited by the adverse PCP-like behavioral side effects that are caused by these drugs. It is expected that the glycine receptor antagonists that are the subject of this invention will be highly effective in preventing chronic pain in mice induced by injecting formalin subcutaneously into the hindpaw of the animals. Because the glycine/excitatory amino acid antagonists of this invention are expected to be free of PCP-like side effects, these drugs are highly useful in preventing or treating chronic pain without causing PCP-like adverse behavioral side effects.

The effects of the glycine receptor antagonists of the present invention on chronic pain may be evaluated as follows. Male Swiss/Webster mice weighing 25–35 grams are housed five to a cage with free access to food and water and are maintained on a 12 hour light cycle (light onset at 0800 h). The glycine receptor antagonist is dissolved in DMSO at a concentration of 1–40 and 5–40 mg/ml, respectively. DMSO is used as vehicle control. All drugs are injected intraperitoneally (1 µl/g). The formalin test is performed as described (Dubuisson and Dennis, *Pain* 4:H161–174 (1977)). Mice are observed in a plexiglass cylinder, 25 cm in diameter and 30 cm in height. The plantar surface of one hindpaw is injected subcutaneously with 20 µl of 5% formalin. The degree of pain is determined by measuring the amount of time the animal spends licking the formalin-injected paw during the following time intervals: 0–5' (early phase); 5–10', 10–'15' and 15–'50' (late phase). To test whether the glycine/excitatory amino acid antagonists prevent chronic pain in the test animals, vehicle (DMSO) or drugs dissolved in vehicle at doses of 1 mg/kg to 40mg/kg are injected intraperitoneally 30 minutes prior to the formalin injection. For each dose of drug or vehicle control at least six animals are used.

Compared to vehicle control, it is expected that the intraperitoneal injection of the glycine receptor antagonists 30 minutes prior to formalin injection into the hindpaw will significantly inhibit formalin-induced chronic pain in a dose-dependent manner as determined by the reduction of the time spent licking by the mouse of the formalin injected hindpaw caused by increasing doses of glycine/excitatory amino acid antagonist.

Compositions within the scope of this invention include all compositions wherein the compounds of the present invention are contained in an amount which is effective to achieve its intended purpose. While individual needs vary, determination of optimal ranges of effective amounts of each component is with the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for anxiety disorders, e.g., generalized anxiety disorder, phobic disorders, obsessional compulsive disorder, panic disorder, and post traumatic stress disorders. Preferably, about 0.01 to about 10 mg/kg is orally administered to treat or prevent such disorders. For intramuscular injection, the dose is generally about one-half of the oral dose. For example, for treatment or prevention of anxiety, a suitable intramuscular dose would be about 0.0025 to about 15 mg/kg, and most preferably, from about 0.01 to about 10 mg/kg.

In the method of treatment or prevention of neuronal loss in ischemia, brain and spinal cord trauma, hypoxia, hypoglycemia, and surgery, as well as for the treatment of Alzheimer's disease, amyotrophic lateral sclerosis, Huntington's disease and Down's Syndrome, or in a method of treating a disease in which the pathophysiology of the disorder involves hyperactivity of the excitatory amino acids or NMDA receptor-ion channel related neurotoxicity, the pharmaceutical compositions of the invention may comprise the compounds of the present invention at a unit dose level of about 0.01 to about 50 mg/kg of body weight, or an equivalent amount of the pharmaceutically acceptable salt thereof, on a regimen of 1–4 times per day. When used to treat chronic pain or to induce anesthesia, the compounds of the invention may be administered at a unit dosage level of from about 0.01 to about 50 mg/kg of body weight, or an equivalent amount of the pharmaceutically acceptable salt thereof, on a regimen of 1–4 times per day. Of course, it is understood that the exact treatment level will depend upon the case history of the animal, e.g., human being, that is treated. The precise treatment level can be determined by one of ordinary skill in the art without undue experimentation.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Basic salts are formed by mixing a solution of the particular 4-hydroxy-3-nitro-1, 2-dihydroquinolin-2-one of the present invention with a solution of a pharmaceutically acceptable non-toxic base such as sodium hydroxide, potassium hydroxide, choline hydroxide, sodium bicarbonate, sodium carbonate, Tris and the like.

The pharmaceutical compositions of the invention may be administered to any animal which may experience the beneficial effects of the compounds of the invention. Foremost among such animals are humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal or ocular routes. Alternatively, or concurrently, administration may be by the oral route. The dosage administered will be dependent upon the age, health, and weight of the recipient, kind of concurrent treatment, if any, frequency of treatment, and the nature of the effect desired.

When the compositions of the invention are administered ocularly, one may achieve either local or systemic administration. For example, the compositions of the present invention may be administered in the form of eye drops which are substantially isotonic with tear fluid to achieve systemic administration. Preferably, such compositions will also comprise a permeation-enhancing agent which aids the systemic absorption of the compounds of the present invention. See, U.S. Pat. No. 5,182,258. Alternatively, the compositions of the invention may be administered ocularly to treat or prevent optic nerve degeneration. In this embodiment, the compounds of the present invention are administered in the form of eye drops, as disclosed above, or may be injected into the vicinity of the optic nerve. In the alternative, thin ocular implant. s may be employed which slowly release the compounds of the present invention.

In addition to the pharmacologically active compounds, the new pharmaceutical preparations may contain suitable pharmaceutically acceptable carriers comprising excipients and auxiliaries which facilitate processing of the active compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, are present at a concentration of from about 0.01 to 99 percent, together with the excipient.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water- soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension include, for example, sodium carboxymethyl cellulose, sorbitol, and/or dextran. Optionally, the suspension may also contain stabilizers.

The characterization of glycine binding sites in vitro has been difficult because of the lack of selective drug ligands. Thus, the glycine ligands of the present invention may be used to characterize the glycine binding site. Particularly preferred substituted and unsubstituted 4-hydroxy-3-nitro-1,2-dihydroquinolines which may be used for this purpose are isotopically, e.g. radiolabelled derivatives, e.g. where one or more of the atoms are replaced with $^3H$, $^{11}C$, $^{14}C$, $^{15}N$, or $^{18}F$.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLES

Example 1

Synthesis of 3-Nitro4-hydroxy-1,2-dihydroquinolin-2-one

To a mixture of 1.45 g (9.00 mmol) of 2,4-dihydroxyquinoline (Aldrich) in 10 mL of glacial acetic acid was added 2.5 mL of $HNO_3$ (69–71%). The mixture was heated at 90° C. for 5 min to become a red solution, then a precipitate was observed in the solution. The mixture was cooled to room temperature, then was added 40 mL of water and the mixture was stirred for 20 min. The mixture was filtered and washed with water, dried to leave 1.54 g (83%) of title compound as a yellow solid, mp 216° C. (decomposed, lit: Buckle, D. R., et al., *J. Med. Chem.* 18:726–732 (1975), 216° C.). $^1H$ NMR ($CDCl_3$+DMSO-$d_6$), 7.013 (t, 1, J=7.5), 7.105 (d, 1, J=7.5), 7.396 (t, 1, J=7.2), 7.877 (d, 1, 7.8), 11.72 (mb 1).

Example 2

Synthesis of 3, 6-Dinitro-4-hydroxy-1,2-dihydroquinolin-2-one

A solution of 724 mg (3.51 retool) of 3-nitro-4-hydroxy-1,2-dihydroquinolin-2-one and 401 mg (3.97 retool) of $KNO_3$ in 4 mL of 96% $H_2SO_4$ was stirred in an ice-bath for 30 min, then 25° C. for 20 h. The solution was added into 25 mL of ice-water to give a yellow precipitate and the mixture was stirred for 1 h, filtered and washed with water, and dried to leave 602 mg (68%) of title compound as a yellow solid, mp 197°–198° C. (decomposed, lit (Buckle et al., supra) 199° –200° C.). $^1H$ NMR ($CDCl_3$+DMSO-$d_6$), 7.114 (d, 1, J=9.12), 7.980 (dd, 1, J=2.27, 9.13), 8.628 (d, 1, J=2.28), 12.13 (mb, 1).

Example 3

Synthesis of 5,7-Dichloro-2,4-dihydroxyquinoline

A solution of 3.2 g (20 mmol) of 3,5-dichloroaniline and 6.4 g (40 mmol) of diethylmalonate was heated at 180° C. for 1 h. The solution was cooled to room temperature, diluted by 5 mL of methanol and the mixture was filtered. The flitrate was mixed with 3.0 g of $Na_2CO_3$ and 10 mL of water and refluxed for 1 h. The mixture was filtered and the flitrate was acidified by aqueous 2N HCl in ice-bath to pH=1. The mixture was filtered and washed with water, and dried to leave a white solid. The solid was mixed with 20 mL of polyphosphoric acid and heated at 140° C. for 3 h. The solution was cooled to room temperature and diluted with 25 mL of aqueous 1N HCl. The mixture was stirred for 4 h, then neutralized with aqueous 20% NaOH to pH=4. It was filtered and washed with water, dried to leave 1.1 g of white solid. The solid was boiled with 40 mL of acetic acid, filtered and dried to leave 762 mg (16%) of the title compound as a white solid, mp 360°–361 ° C. (decomposed). $^1H$ NMR ($CDCl_3$+DMSO-$d_6$), 5.447 (s, 1), 6.620 (d, 1, J=1.84), 6.804 (d, 1, J=1.86), 10.915 (sb, 1). MS, 229 (100, M$^+$), 187 (80), 160 (30), 124 (20). High resolution MS, Calcd for $C_9H_5^{35}Cl_2NO_2$ 228.9694, found 228.9709.

Example 4

Synthesis of 5, 7-Dichloro-3-nitro-4-hydroxy-1,2-dihydroquinolin-2-one

To a mixture of 534 mg (2.32 mmol) of 5,7-dichloro-2, 4-di-hydroxy-1,2-dihydroquinolin-2-one in 3 mL of glacial acetic acid was added 0.7 mL of $HNO_3$ (69–71%) and the mixture was heated at 90° C. for 30 min. The mixture was cooled to room temperature, filtered and washed with water, and dried to leave 562 mg (88%) of the title compound as a yellow solid, mp 170°–171 ° C. (decomposed). $^1H$ NMR ($CDCl_3$+DMSO-$d_6$), 6,909 (d, 1, J=1.86), 6,997 (d, 1, J=1.84), 11.993 (sb, 1). MS, 274 (35, M$^+$), 258 (20), 241 (100), 160 (50). High resolution MS, Calcd for $C_9H_4^{35}Cl_2N_2O_4$ 273.9544, found 273.9551.

Example 5

Synthesis of 5, 7-Dichloro-3, 6-dinitro-4-hydroxy-1, 2-dihydroquinolin-2-one and 5,7-dichloro-3, 8-dinitro-4-hydroxy-1,2-dihydroquinolin-2-one A solution of 136 mg (0.494 mmol) of 5,7-dichloro-4-hydroxy-3-nitro-1,2-dihydroquinolin-2-one and 62 mg (0.60 mmol) of $KNO_3$ in 1 mL of 96% $H_2SO_4$ was stirred in an ice-bath for 30 min, then 25° C. overnight. To the solution was added 2 mL of ice-water and the precipitate was filtered, washed with water and dried to leave 142 mg (89%) of yellow solid which is a mixture of the title compounds, mp 212°–214° C. $^1$H NMR ($CDCl_3$ +DMSO-$d_6$), 7.218 (s, 0.8), 7.319 (s, 0.2), 12.5 (mb, 1). MS, 319 (100, M$^+$), 303 (40), 261 (50), 243 (40), 232 (50), 215 (70), 185 (50). High resolution Calcd for $C_9H_3{}^{35}Cl_2N_3O_6$, 318.9394, found 318.9400.

Example 6

Synthesis of 5,6-Dichloro-2,4-dihydroxyquinoline and 6,7-dichloro-2,4-dihydroxyquinoline A solution of 9.75 g (60.2 mmol) of 3,4-dichloroaniline and 21.1 g (132 mmol) of diethyl malonate was heated at 180° C. under N2 for 30 h. It was cooled to room temperature, filtered and washed with 10 mL of methanol. The filtrate was mixed with 15 g of $Na_2CO_3$, 30 mL of water and 10 mL of methanol and refluxed for 1 h. The mixture was acidified with aqueous 6N HCl in an ice-bath to pH=1. The precipitate was filtered and washed with water, and dried to leave a white solid (9.4 g). $^1$H NMR ($CDCl_3$+DMSO-$d_6$), 3.099 (s, 2), 7.028 (d, 1, J=8.75), 7.128 (dd, 1, J=2.26, 8.70), 7.619 (d, 1, J=2.23), 9.800 (s, 1). The solid was mixed with 100 mL of polyphosphoric acid and heated at 140° C. for 3 h. The solution was cooled to room temperature and diluted with 100 mL of aqueous 1N HCl and 300 mL of water in an ice-bath. The mixture was then neutralized in an ice-bath with aqueous 20% NaOH to pH=4. The mixture was filtered and washed with water, dried to leave 8.2 g (95%) of pale-yellow solid as a mixture of the title compounds. $^1$H NMR ($CDCl_3$+DMSO-$d_6$), 5,6-dichloro- derivative: 5.5 13 (s, 1), 7.050 (s, 1), 7.510 (s, 1), 10.86 (sb, 1); 5,7-dichloro-derivative: 5.597 (s, 1), 6.846 (d, 1, J=9.0), 7.066 (d, 1, J=9.0), 10.90 (sb, 1); ratio=1:1. A portion (800 mg) of the mixture was dissolved in 15 mL of aqueous 1N NaOH and filtered. The flitrate was acidified by aqueous 2N HCl to pH=8.2 to give a solid precipitate. It was filtered, washed with water and dried to leave a white solid. $^1$H NMR shows the ratio again to be 1:1. The aqueous solution was acidified to pH=8.0 to give more precipitate. It was filtered, washed with water and dried to leave a white solid. $^1$H NMR shows again the ratio to be 1:1. The aqueous solution was acidified to pH=4.0 to give more precipitate. It was filtered, washed with water and dried to leave a white solid. $^1$H NMR shows the ratio of the 5,6-dichloro- derivative to the 6,7-dichloro-derivative to be 1:0.7.

Example 7

Synthesis of 6, 7-Dichloro-3-nitro-4-hydroxy-1,2-dihydroquinolin-2-one

To a mixture of 1.25 g (5.43 mmol) of 5,6-dichloro-2,4-dihydroxyquinoline and 6,7-dichloro-2,4-dihydroxyquinoline in 8 mL of glacial acetic acid was added 1.5 mL of $HNO_3$ (69–71%) and the mixture was heated at 90° C. for 2 h. The mixture was cooled to room temperature, filtered and washed with water, and dried to leave 280 mg (19%) of the title compound as a yellow solid, mp 235°–236° C. (decomposed). $^1$H NMR ($CDCl_3$+DMSO-$d_6$), 7.362 (s, 1), 8.039 (s, 1), 11.369 (s, 1). MS, 274 (50, M$^+$), 214 (100), 187 (18), 160 (20). High resolution MS, Calcd for $C_9H_4{}^{35}Cl_2N_2O_4$ 273.9544, found 273.9548.

Example 8

Synthesis of 6,7-Dichloro-3,5-dinitro-4-hydroxy-1, 2-dihydroquinolin-2-one or 6,7-dichloro-3,8-dinitro-4-hydroxy-1,2-dihydroquinolin-2-one A solution of 143 mg (0.520 mmol) of 6,7-dichloro-3-nitro-4-hydroxy-1,2-dihydroquinolin-2-one and 210 mg (2.07 mmol) of $KNO_3$ in 1 mL of 96% $H_2SO_4$ was stirred in an ice-bath for 1 h, then 25° C. for 48 h. To the solution was added 4 mL of ice-water and the precipitate was filtered, washed with water and dried to leave 138 mg (84%) of yellow solid which is either one of the two title compounds, mp 195°–196° C. $^1$H NMR ($CDCl_3$+DMSO-$d_6$), 8.120 (s, 1). MS, 319 (100, M$^+$), 303 (45) 259 (30), 243 (35), 232 (40), 215 (60), 199 (70). High resolution MS, Calcd for $C_9H_3{}^{35}Cl_2N_3O_6$, 318.9394, found 318.9390.

Having now fully described this invention, it will be understood to those of ordinary skill in the art that the same can be performed within a wide and equivalent range of conditions, formulations and other parameters without affecting the scope of the invention or any embodiment thereof. All patents and publications cited herein are fully incorporated by reference herein in their entirety.

What is claimed is:

1. A method of treating neuronal loss associated with stroke, ischemia, CNS trauma, hypoglycemia or surgery, comprising administering to an animal in need of such treatment an effective amount of a compound of the Formula

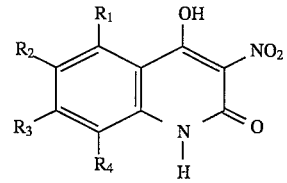

or a pharmaceutically acceptable salt thereof:
wherein $R_1$–$R_4$ may be hydrogen, nitro, amino, halo, haloalkyl, cyano, alkyl, alkenyl, alkynyl, azido, acylamino, sulfonyl, aryl or alkoxy.

2. The method of claim 1, wherein said compound is 4-hydroxy-3-nitro-1,2-dihydroquinolin-2-one.

3. The method of claim 1, wherein said compound is 5,7-dichloro-4-hydroxy-3-nitro-1,2-dihydroquinolin-2-one.

4. The method of claim 1, wherein said neuronal loss occurs as a result of air bubbles that lodge in the brain during or immediately after surgery.

5. The method of claim 1, wherein said neuronal loss occurs as a result of cardiopulmonary bypass surgery.

6. The method of claim 1, wherein said neuronal loss occurs as a result of carotid endarterectomy surgery.

7. The method of claim 1, wherein said neuronal loss occurs as a result of multiple strokes resulting in dementia.

8. A method of treating adverse consequences of hyperactivity of excitatory amino acids, comprising administering to an animal in need of such treatment an effective amount of a compound of the Formula

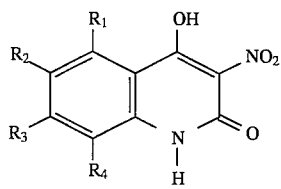

or a pharmaceutically acceptable salt thereof;
wherein $R_1$–$R_4$ may be hydrogen, nitro, amino, halo, haloalkyl, cyano, alkyl, alkenyl, alkynyl, azido, acylamino, sulfonyl, aryl or alkoxy.

9. The method of claim 8, wherein said compound is 4-hydroxy-3-nitro-1,2-dihydroquinolin-2-one.

10. The method of claim 8, wherein said compound is 5,7-dichloro-4-hydroxy-3-nitro-1,2-dihydroquinolin-2-one.

11. A method of treating chronic pain, comprising administering to an animal in need of such treatment an effective amount of a compound of the Formula:

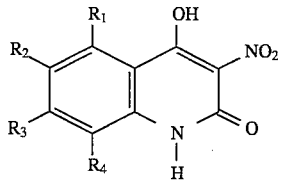

or a pharmaceutically acceptable salt thereof;
wherein $R_1$–$R_4$ may be hydrogen, nitro, amino, halo, haloalkyl, cyano, alkyl, alkenyl, alkynyl, azido, acylamino, sulfonyl, aryl or alkoxy.

12. The method of claim 11, wherein said compound is 4-hydroxy-3-nitro-1,2-dihydroquinolin-2-one.

13. The method of claim 11, wherein said compound is 5,7-dichloro-4-hydroxy-3-nitro-1,2-dihydroquinolin-2-one.

14. A method of treating anxiety, comprising administering to an animal in need of such treatment an effective amount of a compound of the Formula

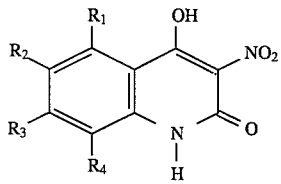

or a pharmaceutically acceptable salt thereof;

wherein $R_1$–$R_4$ may be hydrogen, nitro, amino, halo, haloalkyl, cyano, alkyl, alkenyl, alkynyl, azido, acylamino, sulfonyl, aryl or alkoxy.

15. The method of claim 14, wherein said compound is 4-hydroxy-3-nitro-1,2-dihydroquinolin-2-one.

16. The method of claim 14, wherein said compound is 5,7-dichloro-4-hydroxy-3-nitro-1,2-dihydroquinolin-2-one.

17. A method of treating convulsions, comprising administering to an animal in need of such treatment an effective amount of a compound of the Formula

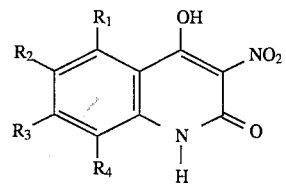

or a pharmaceutically acceptable salt thereof;
wherein $R_1$–$R_4$ may be hydrogen, nitro, amino, halo, haloalkyl, cyano, alkyl, alkenyl, alkynyl, azido, acylamino, sulfonyl, aryl or alkoxy.

18. The method of claim 17, wherein said compound is 4-hydroxy-3-nitro-1,2-dihydroquinolin-2-one.

19. The method of claim 17, wherein said compound is 5,7-dichloro-4-hydroxy-3-nitro-1,2-dihydroquinolin-2-one.

20. A method of inducing anesthesia, comprising administering to an animal in need of such treatment an effective amount of a compound of the Formula:

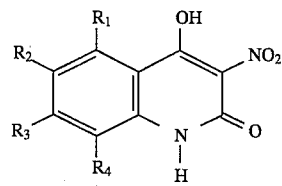

or a pharmaceutically acceptable salts thereof;
wherein $R_1$–$R_4$ may be hydrogen, nitro, amino, halo, haloalkyl, cyano, alkyl, alkenyl, alkynyl, azido, acylamino, sulfonyl, aryl or alkoxy.

21. The method of claim 20, wherein said compound is 4-hydroxy-3-nitro-1,2-dihydroquinolin-2-one.

22. The method of claim 20, wherein said compound is 5,7-dichloro-4-hydroxy-3-nitro-1,2-dihydroquinolin-2-one.

* * * * *